(12) United States Patent
McFarlane

(10) Patent No.: US 8,398,666 B2
(45) Date of Patent: *Mar. 19, 2013

(54) PENETRATING TIP FOR TROCAR ASSEMBLY

(75) Inventor: Richard H. McFarlane, Singer Island, FL (US)

(73) Assignee: Teleflex Medical Incorporated, Limerick, PA (US)

( * ) Notice: Subject to any disclaimer, the term of this patent is extended or adjusted under 35 U.S.C. 154(b) by 126 days.

This patent is subject to a terminal disclaimer.

(21) Appl. No.: 11/115,094

(22) Filed: Apr. 26, 2005

(65) Prior Publication Data

US 2005/0251190 A1    Nov. 10, 2005

Related U.S. Application Data

(63) Continuation-in-part of application No. 10/120,895, filed on Apr. 11, 2002, now Pat. No. 6,884,253, which is a continuation-in-part of application No. 09/859,009, filed on May 16, 2001, now Pat. No. 6,478,806.

(60) Provisional application No. 60/204,396, filed on May 16, 2000.

(51) Int. Cl.
    *A61B 17/34* (2006.01)

(52) U.S. Cl. .................................................. 606/185

(58) Field of Classification Search .................. 606/184, 606/185; 600/566, 567; 604/264, 164.12
    See application file for complete search history.

(56) References Cited

U.S. PATENT DOCUMENTS

| 3,173,200 A | | 3/1965 | Dunmire et al. | |
|---|---|---|---|---|
| 3,613,684 A | * | 10/1971 | Sheridan | 604/264 |
| 3,705,577 A | | 12/1972 | Sierra | |
| 3,789,852 A | * | 2/1974 | Kim et al. | 604/104 |
| 4,535,773 A | | 8/1985 | Yoon | |
| 4,561,445 A | | 12/1985 | Berke et al. | |
| 4,573,448 A | * | 3/1986 | Kambin | 606/170 |
| 4,654,030 A | | 3/1987 | Moll et al. | |

(Continued)

FOREIGN PATENT DOCUMENTS

| CN | 206928 U | 1/1991 |
|---|---|---|
| DE | 195 12 607 A1 | 10/1996 |

(Continued)

*Primary Examiner* — S. Thomas Hughes
*Assistant Examiner* — Sarah Simpson
(74) *Attorney, Agent, or Firm* — Baker Hostetler LLP

(57) ABSTRACT

A tissue penetrating instrument of the type used in the medical field and which may or may not be embodied in the form of an obturator associated with a trocar assembly, wherein the instrument includes an elongated shaft having a penetrating tip mounted on one end thereof. The penetrating tip includes a base secured to the one end of the shaft and a distal extremity spaced longitudinally outward from the base and formed into an apex which may be defined by a point or other configuration specifically structured to facilitate penetration or puncturing of bodily tissue. The apex may be substantially aligned with a linear extension of the central longitudinal axis of the shaft or alternatively, may be spaced laterally outward or off-set from the central longitudinal axis of the shaft. The penetrating tip further includes an exterior surface extending continuously between the apex and the base and configured to facilitate puncturing of the tissue and an enlargement of an access opening formed in the tissue, in a manner which facilitates separation of the tissue and minimizes cutting, severing or otherwise damaging the contiguous bodily tissue surrounding the access opening.

3 Claims, 9 Drawing Sheets

U.S. PATENT DOCUMENTS

| | | | |
|---|---|---|---|
| 4,808,157 A | 2/1989 | Coombs | |
| 4,869,717 A | 9/1989 | Adair | |
| 5,009,643 A | 4/1991 | Reich et al. | |
| 5,057,082 A * | 10/1991 | Burchette, Jr. | 604/164.06 |
| 5,057,085 A * | 10/1991 | Kopans | 604/173 |
| 5,114,407 A | 5/1992 | Burbank | |
| 5,116,353 A | 5/1992 | Green | |
| 5,139,485 A | 8/1992 | Smith et al. | |
| 5,183,464 A | 2/1993 | Dubrul et al. | |
| 5,215,526 A | 6/1993 | Deniega et al. | |
| 5,224,951 A | 7/1993 | Freitas | |
| 5,224,952 A | 7/1993 | Deniega et al. | |
| 5,254,106 A | 10/1993 | Feaster | |
| 5,256,147 A | 10/1993 | Vidal et al. | |
| 5,256,149 A | 10/1993 | Banik et al. | |
| 5,263,937 A | 11/1993 | Shipp | |
| 5,275,583 A * | 1/1994 | Crainich | 604/264 |
| 5,312,360 A | 5/1994 | Behl | |
| 5,314,417 A | 5/1994 | Stephens et al. | |
| 5,318,580 A | 6/1994 | Gresl, Jr. | |
| 5,352,206 A | 10/1994 | Cushieri et al. | |
| 5,372,588 A | 12/1994 | Farley et al. | |
| 5,376,076 A | 12/1994 | Kaali | |
| 5,387,197 A | 2/1995 | Smith et al. | |
| 5,391,156 A | 2/1995 | Hildwein et al. | |
| 5,405,328 A | 4/1995 | Vidal et al. | |
| 5,478,328 A | 12/1995 | Silverman et al. | |
| 5,569,288 A * | 10/1996 | Yoon | 606/185 |
| 5,569,292 A | 10/1996 | Scwemberger et al. | |
| 5,601,559 A | 2/1997 | Melker et al. | |
| 5,624,459 A | 4/1997 | Kortenbach et al. | |
| 5,634,937 A | 6/1997 | Mollenauer et al. | |
| 5,674,237 A | 10/1997 | Ott | |
| 5,676,681 A | 10/1997 | Yoon | |
| 5,690,663 A | 11/1997 | Stephens | |
| 5,730,754 A | 3/1998 | Obenchain | |
| 5,792,142 A | 8/1998 | Galitzer | |
| 5,800,451 A | 9/1998 | Buess et al. | |
| 5,807,317 A | 9/1998 | Krech, Jr. | |
| 5,807,338 A | 9/1998 | Smith et al. | |
| 5,843,039 A * | 12/1998 | Klemm | 604/164.01 |
| 5,882,340 A | 3/1999 | Yoon | |
| 5,916,232 A * | 6/1999 | Hart | 606/185 |
| 5,984,919 A | 11/1999 | Hilal et al. | |
| 5,984,941 A | 11/1999 | Wilson et al. | |
| 6,056,766 A | 5/2000 | Thompson et al. | |
| 6,063,099 A | 5/2000 | Danks et al. | |
| D426,635 S | 6/2000 | Haberland et al. | |
| 6,099,544 A | 8/2000 | Wolf et al. | |
| 6,106,539 A | 8/2000 | Fortier | |
| 6,168,607 B1 | 1/2001 | Wattiez et al. | |
| 6,203,557 B1 | 3/2001 | Chin | |
| D443,360 S | 6/2001 | Haberland et al. | |
| D449,887 S | 10/2001 | Haberland et al. | |
| 6,325,811 B1 * | 12/2001 | Messerly | 606/169 |
| 6,884,253 B1 | 4/2005 | McFarlane | |

FOREIGN PATENT DOCUMENTS

| | | |
|---|---|---|
| FR | 2073688 | 12/1970 |
| JP | 59-133205 | 9/1984 |
| JP | 63-200749 | 8/1988 |
| JP | 9-108233 | 4/1997 |
| JP | 10-512169 | 11/1998 |
| WO | WO 98/07399 | 2/1998 |

\* cited by examiner

PENETRATING TIP FOR TROCAR ASSEMBLY

CLAIM OF PRIORITY

The present application is a Continuation-In-Part application of previously filed, now application having Ser. No. 10/120,895, which was filed on Apr. 11, 2002 and which is set to issue as U.S. Pat. No. 6,884,253 on Apr. 26, 2005, which itself was filed as a Continuation-In-Part application of a previously filed, then application, namely, Ser. No. 09/859,009 filed on May 16, 2001, which matured into U.S. Pat. No. 6,478,806, and which in turn, was based on and a claim to priority made under 35 U.S.C. Section 119(e) to an earlier filed, U.S. provisional patent application having Ser. No. 60/204,396 and a filing date of May 16, 2000, all of which are incorporated herein in their entirety by reference.

BACKGROUND OF THE INVENTION

1. Field of the Invention

The present invention is directed towards a medical instrument of the type structured for use in laparoscopic and/or endoscopic surgery such as, but not limited to, a trocar assembly which includes an elongated shaft having a penetrating tip formed on one end thereof. The penetrating tip includes an exterior surface configuration structured to facilitate the forming of an access opening in bodily tissue in a manner which requires a minimum application of an inwardly directed, linear pushing force on the instrument, but rather, which is more responsive to a back and forth or "reciprocal" twisting motion. The configuration of the penetrating tip is at least partially characterized by a perpendicular cross-section of the exterior surface having a substantially elliptical configuration along at least a majority of the tip.

2. Description of the Related Art

In the medical field there are numerous instruments specifically designed to penetrate bodily tissue so as to provide access to internal body cavities or organs. More specifically, a preliminary procedure during the performance of surgery is the creation of an access opening into the body cavity at a predetermined surgical site. In the past, such access openings were formed by the creation of substantially large incisions through the body wall or outer tissue. The size of an incision would depend on the type of surgery, and accordingly, the surgical instruments involved. On completion of the surgical procedure, the large incision would be closed using conventional techniques. However, due to the traumatic nature of such open surgical procedures, the period of time required for the patient to completely heal was significant. In addition, the pain or discomfort during the recuperative period was a serious problem.

Because of the above noted disadvantages, attempts have been made, which were specifically directed towards new surgical procedures as well as instruments utilized in the support of such procedures. More recently, it has become quite common to employ an alternative type of surgery known as laparoscopic and/or endoscopic surgery, wherein one or more small openings, utilizing appropriate penetrating instruments, are formed in a patient's abdomen typically, to provide access into the intended body cavities wherein surgery on a targeted organ or organs may take place. Unlike the large incision required during open surgery, the much smaller access openings facilitate healing following the surgery and as expected, result in significantly less discomfort to the patient.

Depending on the type of laparoscopic surgery being performed, the instrumentation used to form the one or more small access openings may vary. However, common to such medical penetrating instruments is the provision of a sharpened or otherwise configured penetrating tip. By way of example, instrumentation utilized in the performance of laparoscopic surgery are commonly referred to as trocar devices or trocar assemblies. In conventional fashion, a trocar assembly normally includes a trocar sleeve or cannula and an obturator to which the penetrating tip is attached. Utilizing such instrumentation, access is gained to a body cavity or organ by penetrating the bodily tissue defining the exterior wall of the cavity, in order that laparoscopic surgery may be performed.

The obturator, serving as the penetrating instrument, passes along or is positioned within the lumen of the cannula or trocar sleeve. The penetrating tip is formed on the distal end of the obturator and is forced through the skin until entry to the body cavity has been established. The trocar sleeve, is then forced through the perforation, formed by the obturator and the obturator is withdrawn, leaving the trocar sleeve or cannula as an access passage to the intended body cavity or organ. In related laparoscopic or endoscopic surgical techniques, the penetrating instrument may be used with the trocar sleeve or surgical access cannula or may be used as a "stand alone" device to puncture through the skin and underlying bodily tissue. A small access opening is thereby formed and a separate access cannula, catheter or other surgical instrument is inserted into communication with the now accessed body cavity or organ.

The aforementioned, substantially conventional, medical penetrating instruments normally include a penetrating tip having a sharpened point spaced distally from a base which is connected to one end of the obturator or penetrating instrument. Also, the conventional structure of such penetrating tips typically include either a conical or a multi-sided, substantially pyramidal configuration. The design and structuring of penetrating tips for the type of medical instruments described herein is/are important for the efficient formation of the small access opening, as set forth above. However, such penetrating tips should efficiently and cleanly create the access opening in a manner which serves to at least partially dilate or enlarge the opening, as the shaft of the obturator or other penetrating instrument passes through the bodily tissue. It is, of course, equally important that a minimal amount of damage, in terms of severing or cutting, be done to the contiguous body tissue surrounding the access opening during the initial penetration, as well as the enlargement of the access opening, as the penetrating instrument is positioned into direct communication with the intended body cavity or organ.

Accordingly, there is a need in the field of medical instrumentation for an instrument which may be used independently or which may be associated with a trocar assembly and associated components such as, but not limited to, a trocar sleeve, etc. Any such an improved instrument would preferably be designed to include an improved penetrating tip which is structured to facilitate the smooth and/or clean formation of a small access opening through the puncturing of the body wall. The penetrating tip should preferably include an exterior surface, as well as a distal extremity or apex, and a base which are cooperatively structured and efficiently configured. The structuring of these components should be such as to effectively enlarge the access opening, as the penetrating instrument is advanced therethrough into communicating relation with a predetermined body cavity or organ. Further, the disposition, dimension, configuration and overall structure of any such inventive penetrating tip should be such as to form the access opening without causing any unnecessary or inadvertent cutting, severing or like damage to the outer tissue being penetrated or to the internal organs, once the penetrating tip enters the intended body cavity.

SUMMARY OF THE INVENTION

The present invention is intended to address these and other needs in the art and as such, is directed towards a penetrating instrument of the type used in laparoscopic, endoscopic or like, minimally invasive surgical procedures, and which is preferably, but not necessarily, embodied in a trocar assembly. In such embodiment, the trocar assembly includes a trocar housing and a trocar sleeve or cannula having an open distal end communicating with a centrally disposed lumen or passage within the trocar sleeve and within the housing. The trocar assembly further includes an obturator comprising an elongated shaft having a proximal end and an oppositely disposed distal end on which a penetrating tip is either formed or secured. Whether or not embodied in a trocar assembly, the elongated shaft and the penetrating tip of the obturator are specifically structured to create a small access opening in the body wall or outer tissue of a patient so as to establish communication with an internal body cavity or organ on which a surgical procedure is to be performed.

The penetrating instrument of this invention is designed and structured to effectively create the small access opening by penetrating through the skin and underlying body tissue of a patient in a manner which serves to separate and enlarge the created access opening, as the penetrating tip, shaft and/or trocar sleeve pass there-through and into the patient's abdominal body cavity. As explained in greater detail herein, the overall structure, configuration, dimension and disposition of the penetrating instrument is such as to accomplish an effective separation of the bodily tissue being penetrated with a minimal application of an inwardly directed linear force. In doing so, the structure of the penetrating instrument dilates the outer tissue in a manner which minimizes damage to the tissue. Also, the possibility of inadvertently injuring blood vessels, etc. is minimized, as is the possibility of injuring internal organs once the instrument's penetrating tip enters the intended body cavity. More specifically, the instrument of the present invention, whether associated with a trocar assembly or used independently thereof, comprises an obturator having an elongated shaft and a penetrating tip integrally formed on or otherwise secured to the distal end thereof. When in the preferred embodiment of a trocar assembly, the penetrating tip is cooperatively disposed, dimensioned and configured relative to and/or with the trocar sleeve, and in particular, with the open distal end thereof. The penetrating tip includes a base and a distal extremity configured to define an apex. It is pointed out, here, that the term "apex" is meant to include a variety of different configurations, which may vary from a sharpened point to a tapered locale, as may be defined by the converging of the penetrating tip's exterior surface from a base thereof and extending continuously to the distal extremity or apex. In a preferred embodiment of the present invention, described in greater detail herein, the apex of the penetrating tip is disposed coincident to a central longitudinal axis of the elongated obturator shaft. Other embodiments of the present invention contemplate the apex of the penetrating tip being spaced laterally outward or in an off-set, somewhat eccentric position relative to the central longitudinal access of the elongated obturator shaft.

Although it may assume a variety of configurations as further described herein, the penetrating tip of this invention is preferably structured to facilitate the separation of the body tissue and penetration of the body cavity wall or lining in a manner which minimizes damage to the tissue and other risk of injury to the patient. More specifically, the penetrating tip includes an exterior surface, preferably extending between the base and the apex thereof, that comprises a cross section having a "substantially elliptical" configuration. The interior of the penetrating tip may include a variety of different structures, such as being solid, hollow or partially hollow. It is pointed out that the term "substantially elliptical" as used herein to describe the configuration of the cross section of the exterior surface of the penetrating tip is not meant to define a true or precise ellipse, alone. Rather, the term "substantially elliptical" as used herein is meant to include a variety of different configurations, all of which substantially conform to an ellipse. More specifically, the outer circumference or sectional configuration of the exterior surface of the penetrating tip, preferably taken along a plane perpendicular to the central longitudinal access of the shaft, may include one or more curvilinear segments, a combination of curvilinear segments and linear segments or a plurality of linear segments, wherein the various linear and/or curvilinear segments are collectively interconnected in a closed or continuous configuration.

Accordingly, the structure of the instrument of the present invention, whether or not embodied in a trocar assembly, includes an elongated shaft having a penetrating tip with an exterior surface configuration and/or other components thereof, which are cooperatively dimensioned, configured, and disposed to more safely facilitate the formation of an access opening and the dilation of the surrounding bodily tissue during the insertion of the penetrating instrument into the patient. More specifically, the preferred exterior surface configuration of the penetrating tip enters the designated bodily tissue in a manner which minimizes damage and/or cutting or severing of the tissue during the passage of the penetrating tip, as well as an adjacent portion of the shaft and/or trocar sleeve, through the created access opening.

The objects, features and advantages of the present invention noted above, as well as others, will become more clear when the drawings as well as the detailed description of the invention in various embodiments, below, are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
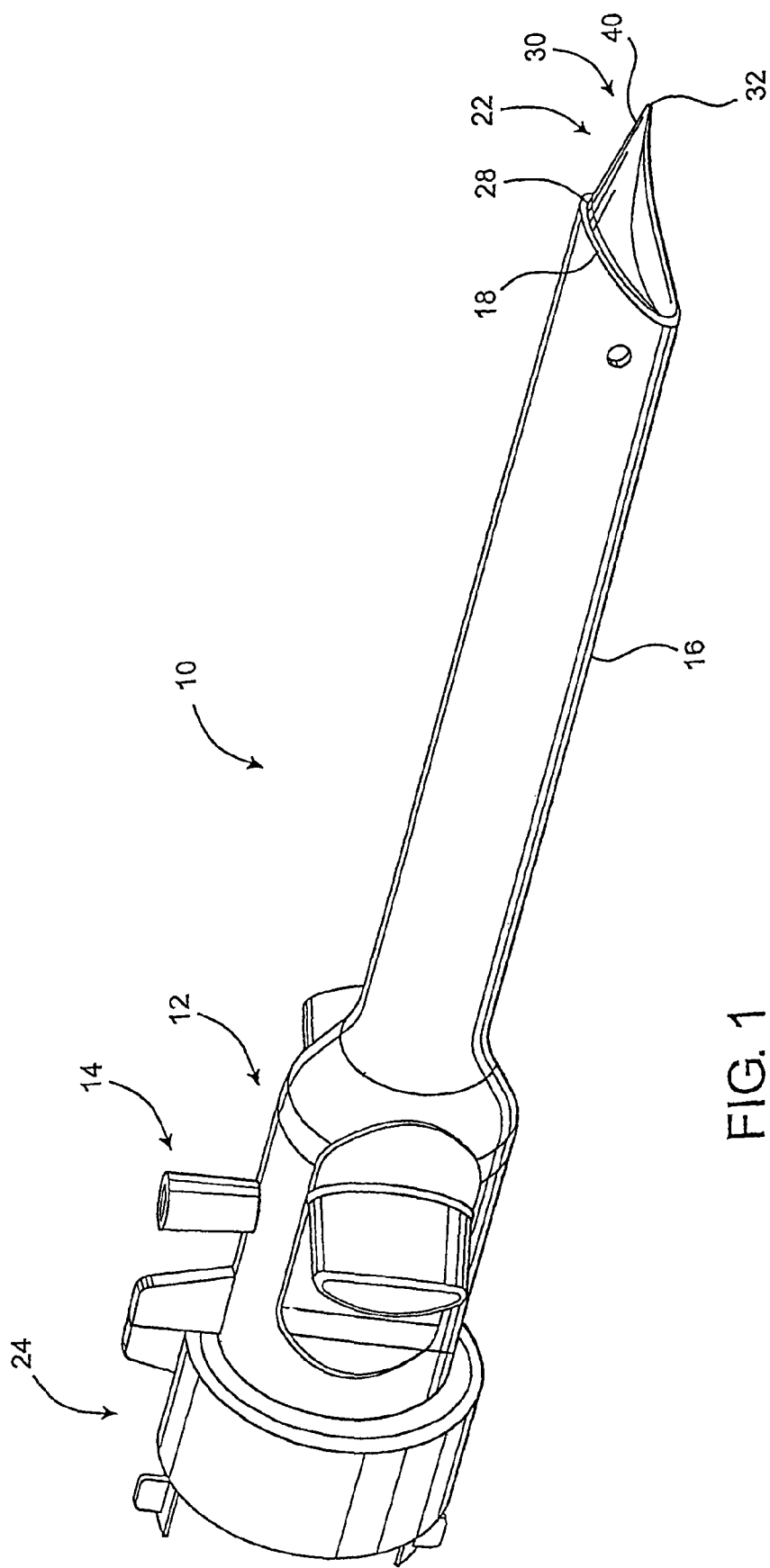
FIG. 1 is a perspective view of a penetrating instrument according to the present invention embodied in a trocar assembly wherein the distal extremity or apex of the penetrating tip is disposed coincident to a central longitudinal axis of the instrument shaft.
Figure 2:
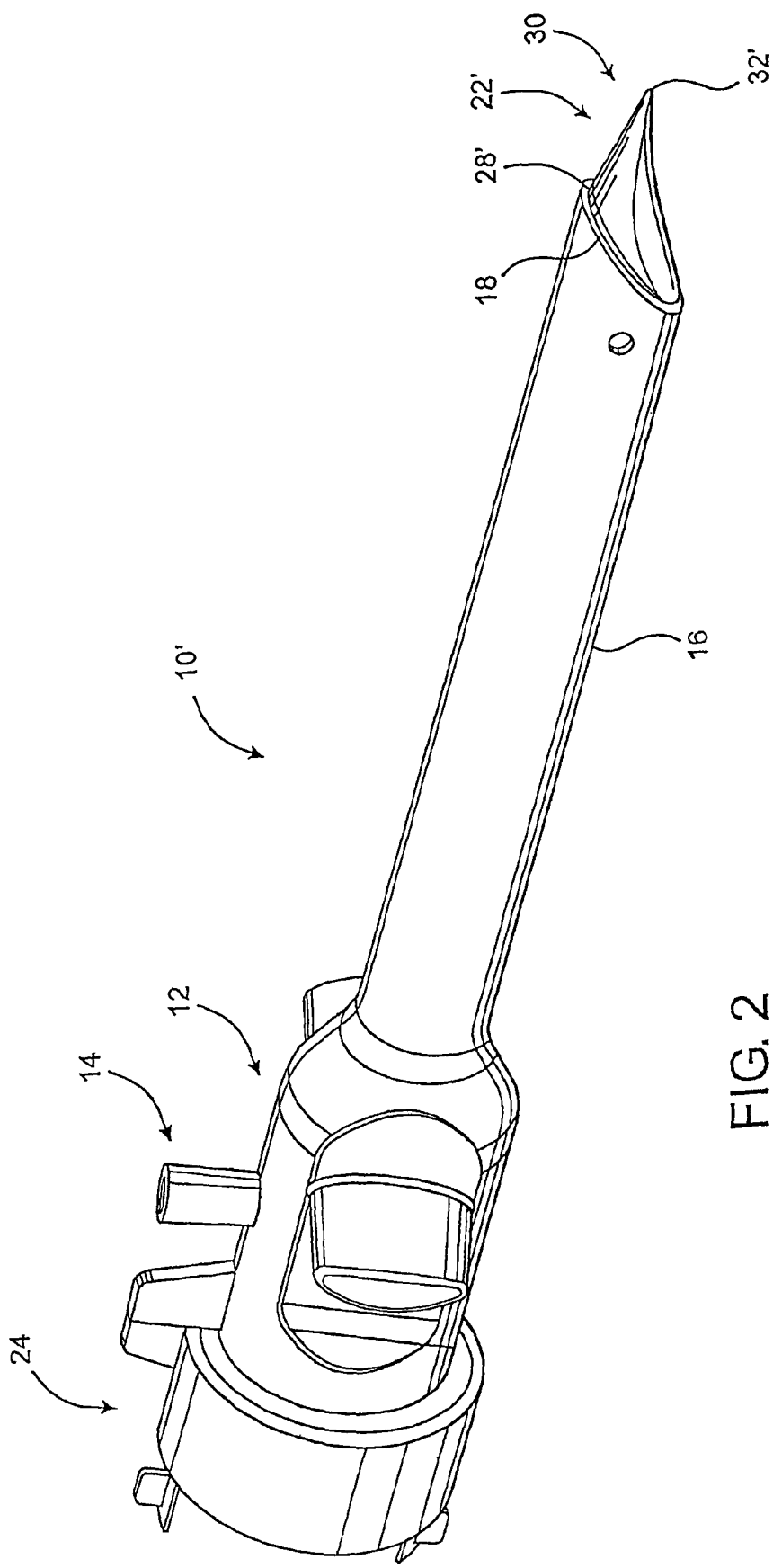
FIG. 2 is a perspective view of another penetrating instrument according to the present invention which is also embodied in a trocar assembly wherein the distal extremity or apex of the penetrating tip is disposed in off-set relation to the central longitudinal axis of the instrument shaft.

As shown in the accompanying Figures, the present invention is directed towards a medical instrument of type structured for use in minimally invasive surgery, such as laparoscopic or endoscopic surgery. Moreover, the instrument of the present invention is preferably, but not necessarily, embodied in a trocar assembly, such as, but in no way limited to, the trocar assemblies shown in FIGS. 1, 2, 12, 14 and 15 and generally indicated as 10 and 10', which assemblies depict a distinctive shape developed by and proprietary to Taut, Inc. of Geneva, Ill.

A trocar assembly, whether that indicated by reference numeral 10, 10' or another, typically includes a trocar housing 12, which may include a connector structure 14 communicating with the interior of the housing 12 and structured to establish interconnection with a supply of fluid, such as carbon dioxide gas, used to inflate a body cavity as typically performed during laparoscopic or endoscopic surgery.

Figure 3:
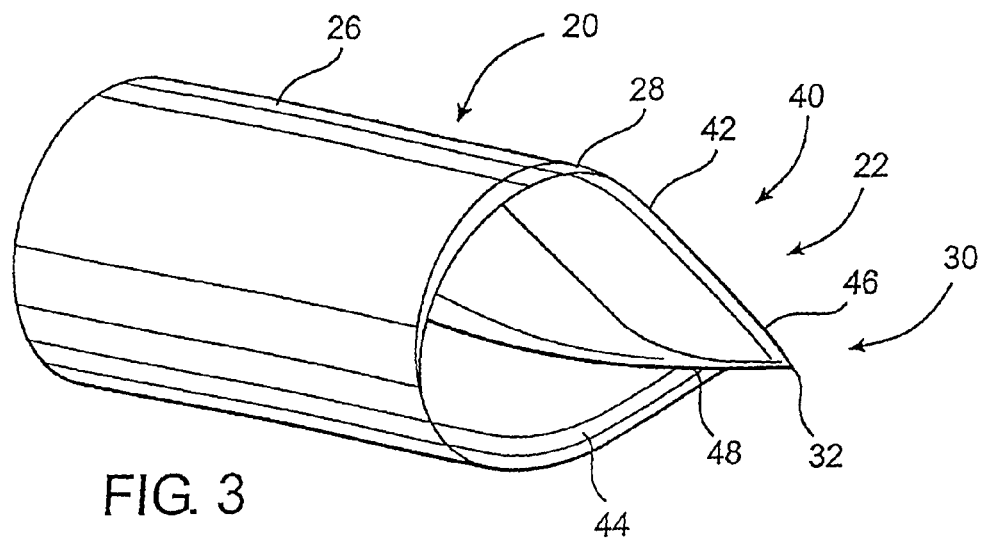
FIG. 3 is a perspective view of another embodiment of a penetrating instrument shown in partial cutaway to better illustrate a penetrating tip associated with the present invention.
Figure 4:
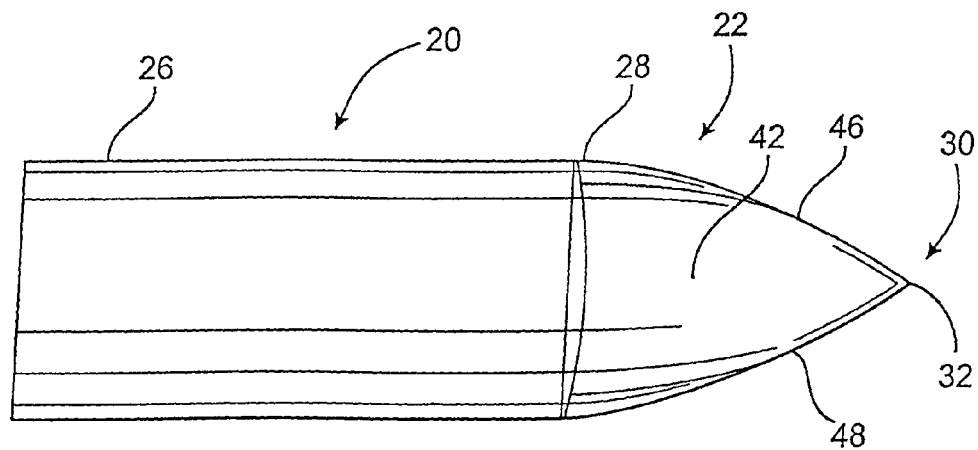
FIG. 4 is a top view of the embodiment of FIG. 3.
Figure 5:
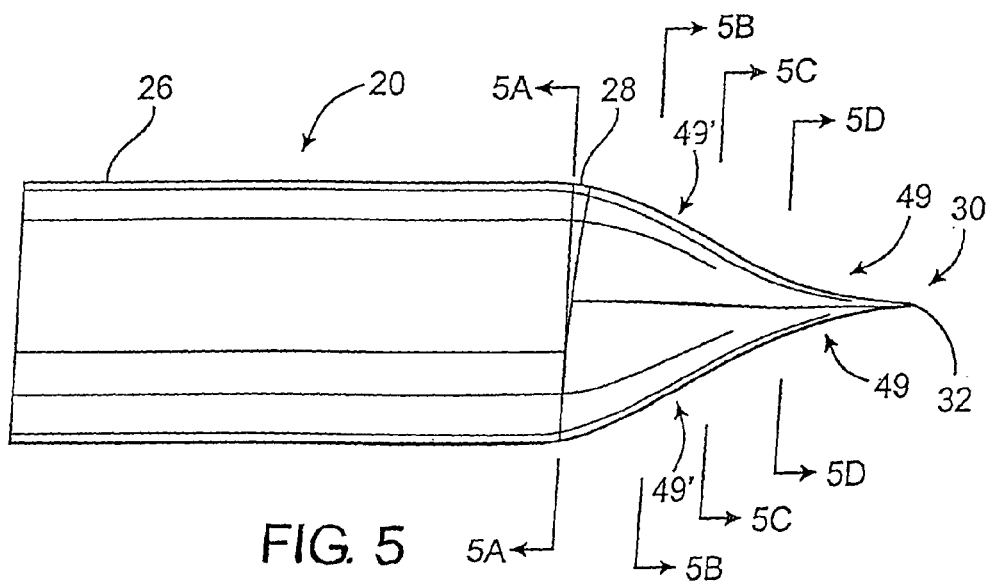
FIG. 5 is a side view of the embodiment of FIGS. 3 and 4.

Trocar assembly 10, 10' also includes an elongated cannula or trocar sleeve 16 dimensioned and structured to removably receive an obturator 20, perhaps best shown in FIGS. 3-5, comprising an elongated shaft 26, along the interior, centrally disposed passage or lumen associated with the sleeve 16. The elongated shaft 26 has a penetrating tip, generally indicated as 22, secured to the distal end of shaft 26 and extending outwardly from a distal open end 18 of the trocar sleeve 16.

It is pointed out that the present invention can be utilized with trocar assemblies, such as 10 and 10' as well as others. While the trocar assemblies shown in FIGS. 1, 2 and 15 appear to be substantially equivalent structures, they differ from one another primarily in the structural configuration of the obturators 20 and 20', and mostly in the structure of the respective penetrating tips 22 and 22'. Also, in each of the embodiments of FIGS. 1, 2 and 15 it is preferred that a mounting hub 24 be connected or secured to a proximal end of the trocar sleeve 16, adjacent or contiguous to the trocar housing 12. As explained hereinafter with primary reference to FIG. 15, the mounting hub 24, secured to a proximal end of the trocar sleeve 16, is structured for mounting or interconnection with an end portion or gripping portion 25 secured to a proximal end 25' of the elongated shaft 26 defining the obturator 20.

As indicated above, the preferred embodiments of the present invention includes the elongated shaft 26, at least partially defining the obturator 20. The shaft 26 or 26' has the distal end integrally formed with or otherwise fixedly connected or secured to the corresponding penetrating tip 22 or 22'. The elongated shaft 26 also has a proximal end 25' which is oppositely disposed to the penetrating tip 22 and which is preferably secured to the gripping portion 25, as noted above and in FIG. 15. While the elongated shafts 26 and 26' are primarily disclosed as including a solid material construction, it is emphasized that either may include a substantially hollow, elongated configuration terminating in the respective penetrating tip 22 or 22'. Alternatively, the penetrating tips 22, 22', of the various embodiments may be formed to be substantially or at least partially hollow. It is to be understood that the penetrating tips 22, 22' may have a variety of other interior structures, such as being solid or at least partially solid.

With primary reference to the embodiment of FIG. 1, FIGS. 3 through 5, and FIG. 14, the shaft 26 of the present invention comprises the penetrating tip 22 having a base 28 integrally or otherwise fixedly secured to the distal end of shaft 26. The opposite end of the penetrating tip 22 terminates in a distal extremity generally indicated as 30. Further, the penetrating tip 22 has an exterior surface extending continuously between the base 28 and the distal extremity 30. The distal extremity 30 may be more specifically defined as an "apex" 32 which may be structured to have, but does not necessarily require, a slightly blunted configuration. However, the apex 32 may also assume a variety of other configurations, such as that shown in the embodiment of FIG. 2 and indicated as 32'. That is, while the term "point" may be used to describe an apex 32, this is not necessarily meant to define a true, sharply pointed structure. On the contrary, in the most preferred embodiments, the apex 32 and/or 32' is structured to be sufficiently blunt to eliminate or significantly reduce the danger of inadvertent puncturing of a patient's organ(s) once the penetrating tip has passed through exterior bodily tissue and entered into the patient's abdominal cavity or other internal cavity. In that the apex 32 and 32' of the inventive penetrating tip may assume a variety of different structural configurations, all of which are intended to facilitate the clean, efficient passage through the outer body wall of a patient, the term apex, rather than point, is used to generically and more accurately describe each of the plurality of tip configurations. Further, the apex 32, 32', regardless of its specific shape, may be defined as a convergent locale of the exterior surface 40 of each of the corresponding penetrating tips 22, 22', as the exterior surface 40 extends from the respective bases 28, 28' to and including the distal extremity 30, 30'.

Still referring to FIGS. 1, 3 through 5, and 14, the more preferred embodiments of the invention comprise the apex 32 being disposed coincident with the central, longitudinal axis 27 of the elongated shaft 26, or more precisely, a linear extension 27' of the central longitudinal axis 27. Further, at least one preferred embodiment comprises the exterior surface 40 including at least two surface segments 42 and 44. As shown in FIGS. 3 and 4, the surface segments 42 and 44 are at least minimally segregated by two at least partially, oppositely disposed and curved edge portions 46 and 48. The edge portions 46 and 48 may be specifically shaped or configured to define cutting and/or dilating edges and extend along at least a portion of the distance between the apex 32, 32' and the base 28, 28'.

For example, the longitudinal curvilinear configuration of the surface segments 42 and 44 are preferably at least partially defined by a complex curve. In turn, the complex curvilinear configuration of each of the surface segments 42 and 44, as viewed longitudinally from the apex 32 to the base 28, comprises at least one substantially concave segment 49 and either a linear or minimally convex curve portion or section 49'. As a result, the overall configuration of the exterior surface of the penetrating tip 22 and its cooperative structuring with the apex 32 facilitates the forming and subsequent enlargement of an access opening in the body wall of a patient, without requiring a heavily applied, inwardly directed, linear pushing force. As such, the access is formed in a manner more of a dilating action, which minimizes cutting of and/or other damage to bodily tissue as the penetrating tip 22, as well as a portion of the shaft 26 and/or sleeve 16 passes through the access opening into a patient's abdominal cavity or other anatomical structure.

In the more preferred embodiments of the present invention, the exterior surface 40 of the penetrating tip 22 has a transverse or perpendicular cross section which is substantially elliptical. It is to be understood that the term "substantially elliptical," when referring to the cross sectional configuration of the exterior surface 40 or the transverse circumferential configuration thereof, is not meant to be limited to a true or precise elliptical configuration, only. To the contrary, the substantially elliptical configuration of the penetrating tip 22 or 22' may assume differently shaped exterior surfaces and yet still be included or intended for inclusion within the phrase "substantially elliptical," as used herein.

Figure 13:
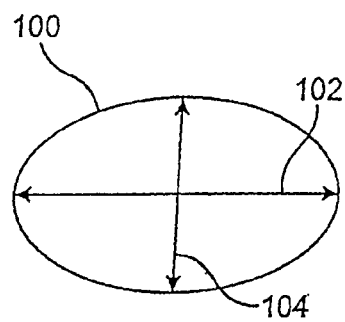
FIG. 13 is a schematic representation of a substantially elliptical configuration representative of a transverse or perpendicular cross-section taken from the exterior surface of a preferred penetrating tip according to the present invention.
Figure 13A:
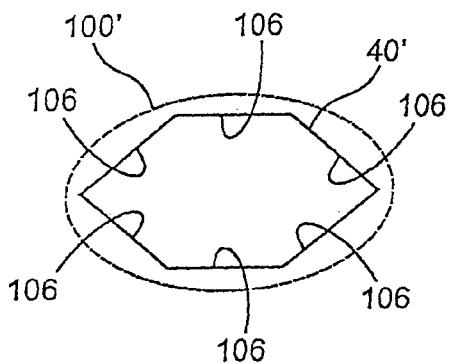
FIG. 13A is a schematic representation of another embodiment of a substantially elliptical configuration representative of a cross section taken from the exterior surface of another penetrating tip according to the present invention.

To better illustrate this, reference will now be made to FIGS. 13, 13A, 13B, 13C, 13D, 13E and 13F. As represented in FIG. 13, there is illustrated a schematic representation of a true or precise elliptical configuration, indicated as 100. This elliptical configuration or ellipse 100 includes a primary longitudinal dimension 102 and a primary transverse dimension 104. Upon reviewing the various embodiments of the penetrating tip disclosed herein (such as 22, 22', 64, etc.,) it will be noted that the size of the cross sectional configuration of the exterior surface 40 will change. In other words, the size of the cross section taken from any given penetrating tip 22, 22', etc. will be larger or smaller dependent upon whether the section is taken closer to the apex 32 or closer to the base 28. This is due to the converging structure of the exterior surface 40 as it extends from the base 28 to the apex 32.

Therefore, with reference to FIG. 13, the term "substantially elliptical" configuration is meant to include variations in the shape of the sectional configuration of the exterior surface 40, due to the fact that either the primary longitudinal dimension 102 may be longer or shorter and/or the primary transverse dimension 104 may be longer or shorter. The result is a sectional configuration of the exterior surface 40, which while not precisely conforming to a precise elliptical configuration, schematically represented as 100, may still be considered a substantially elliptical configuration even though the overall shape is characterized by a flattened, elongated, oblong or other elliptical configuration having a variant shape.

Figure 13B:
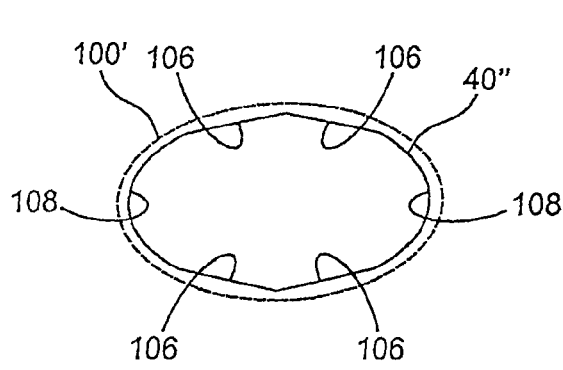
FIG. 13B is a schematic representation of yet another embodiment of a substantially elliptical configuration representative of a cross section taken from the exterior surface of another penetrating tip according to the present invention.
Figure 13C:
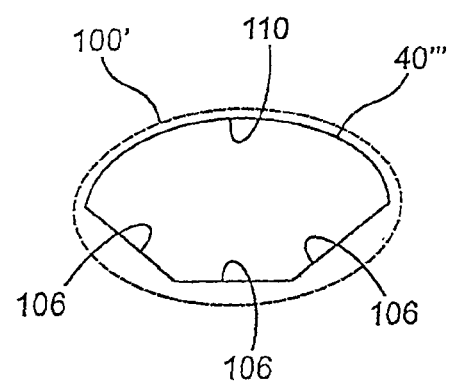
FIG. 13C is a schematic representation of yet another embodiment of a substantially elliptical configuration representative of a cross section taken from the exterior surface of another penetrating tip according to the present invention.
Figure 13D:
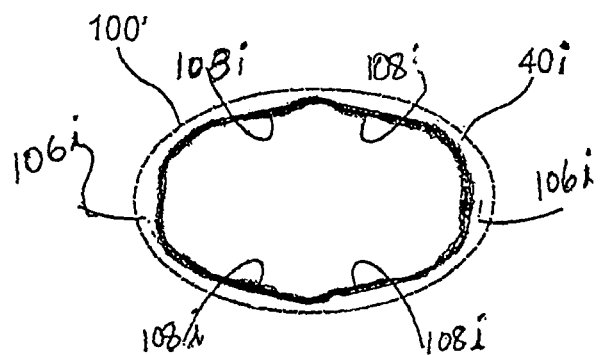
FIG. 13D is a schematic representation of yet another embodiment of a substantially elliptical configuration representative of a cross section taken from the exterior surface of another penetrating tip according to the present invention.
Figure 13E:
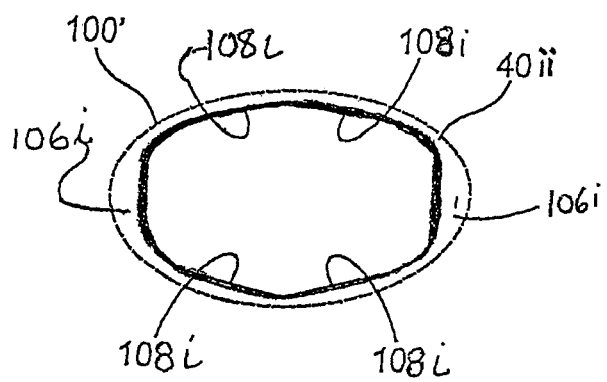
FIG. 13E is also a schematic representation of another potential embodiment of a substantially elliptical configuration representative of a cross section taken from the exterior surface of another penetrating tip according to the present invention.
Figure 13F:
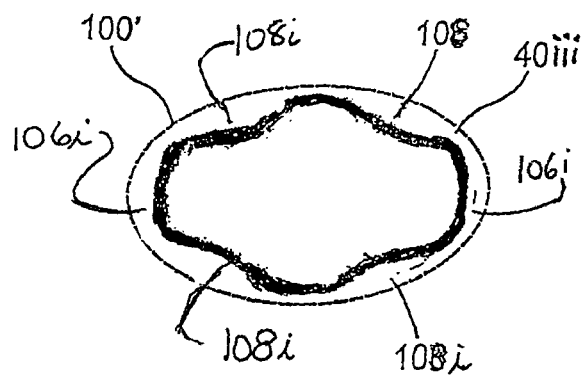
FIG. 13F is also a schematic representation of yet another potential embodiment of a substantially elliptical configuration representative of a cross section taken from the exterior surface of another penetrating tip according to the present invention.

In order to further clarify that the intended meaning of the phrase or term "substantially elliptical" when referring to the penetrating tip's exterior surface 40 can apply to varied equivalent or substantially equivalent shapes, reference is now made to FIGS. 13-A, 13-B, 13-C, 13-D, 13-E and 13-F. It is emphasized that schematic representations illustrated in these Figures are intended to be representative only of a plurality of possible "substantially elliptical" configurations which the exterior surface 40 may assume. In these Figures, a true or precise elliptical configuration is indicated in phantom lines and is marked with reference numeral 100' and the exterior surface 40 is shown in a variety of different shapes as schematically represented as 40', 40", 40''', respectively in FIGS. 13A, 13B, 13C, and 40i, 40ii and 40iii, respectively, in FIGS. 13D, 13E and 13F. These Figures illustrate that the specific shape(s) of the representative exterior surface configurations 40', 40", 40''', 40i, etc. generally conform to the true elliptical configuration 100', and therefore, are clearly intended to be included within the generically descriptive term "substantially elliptical." With specific reference to FIG. 13-A, the exterior surface 40' may include a plurality of linear segments 106 interconnected to one another to form a continuous, closed configuration. FIG. 13B is representative of an exterior surface 40" including a plurality of plane curves or more specifically, curvilinear segments 108 connected to a plurality of linear segments 106. The embodiment of FIG. 13C discloses the exterior surface 40''' having at least one elongated plane curve or curvilinear segment 110 interconnected with at least one but preferably a plurality of linear segments 106 to collectively form a continuous, closed configuration. In addition, FIGS. 13D, 13E and 13F illustrate another possible exterior surface 40i, 40ii, 40iii, with a plurality of plane curves or curvilinear segments 108i interconnected with at least one but preferably a plurality of linear segments 106i to form a continuous, closed configuration which also can be said to be substantially elliptical or an equivalent thereto.

Figure 5A:
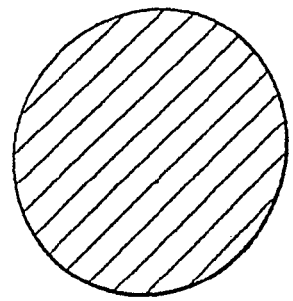
FIG. 5A, 5B, 5C and 5D are sectional views of the embodiment shown in FIG. 5 and taken along lines 5A-5A, 5B-5B, 5C-5C, and 5D-5D, respectively.
Figure 5B:
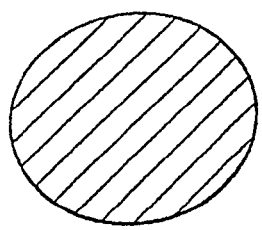
Figure 5C:
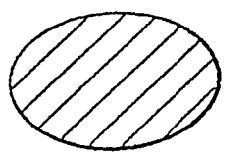
Figure 5D:

In the various preferred embodiments of the penetrating tip 20, 20', 64, etc., of the present invention, the cross sectional configuration of the exterior surface 40 is preferably oriented transverse or perpendicular to the linear extension 27' of the central longitudinal axis 27 of the shaft 26. Also, the cross section or an infinite number of such cross sections extend along at least a majority of the length of the penetrating tip 22, as demonstrated by the schematic and representative cross-sectional configurations in FIGS. 5B, 5C and 5D. Again, it is to be emphasized that the cross sectional configurations of FIGS. 5B through 5D are schematic representations and may be defined by other than a true or precise elliptical configuration such as that disclosed in, but not limited to, FIGS. 13A through 13F. Further by way of reference, the perpendicular cross-sectional configuration of the base 28, taken along the imaginary line 5A-5A, may be, but does not in all cases have to be, defined by a circumferential configuration in the form of a circle. In addition, the base 28 in at least one embodiment may comprise a transitional area or zone between the tip 22 and the distal end of the shaft 26.

It is pointed out that some variation in the substantially elliptical configuration of the cross section of the exterior surface of the penetrating tip may also be due to the existence of the aforementioned, segregating edge portions 46 and 48. As set forth above, the structure of the edge portions 46 and 48 may vary as they may or may not be structured to serve as cutting edges. Accordingly, the opposite ends of each of the representative elliptical configurations shown in FIGS. 5B, 5C, and 5D may also be varied to more accurately represent the inclusion of the edge portions 46 and 48. These edges may vary in cross-sectional configuration from a true cutting edge, as best demonstrated in FIG. 3, to a more rounded configuration, as indicated by the representative elliptical shapes of FIGS. 5B, 5C and 5D.

The various embodiments of the present invention, however, will preferably provide for efficient penetration of the outer bodily tissue and passage there-through in a manner which minimizes the danger of inadvertent puncturing of internal organs. More specifically, such initial penetration and passage of the either of the tips 22 and 22' as well as the respective shafts 26 and 26' and/or sleeve 16 will ideally be accomplished by the exertion of only a minimal amount of a linearly directed, "pushing" force on the instrument. Instead, penetration may be facilitated by applying a twisting motion, and preferably a back and forth or "reciprocal twisting" motion, to the device. In the more preferred embodiment incorporating a somewhat blunted point or apex 32 or 32', the chances are minimized of inadvertently puncturing and/or damaging an internal organ subsequent to the penetrating tip 22 or 22' passing through the exterior bodily tissue and into the body cavity in which the organ is located.

With primary reference now to the embodiment of FIGS. 2 and 6 through 8, one distinguishing structural feature is the location of the apex 32' in an eccentric or laterally spaced, off-set relation to an imaginary co-linear extension of the central longitudinal axis of the shaft 26'. Accordingly, the exterior surface 40 comprises two surface segments 42' and 44' which are non-symmetrical, in that surface segment 42' has a significantly smaller overall dimension than that of the surface segment 44'. As a result, the base 28' has a circumferential configuration preferably defined by an elongated ellipse, schematically represented in FIG. 8A and taken along lines 8A-8A of FIG. 8.

Similar to the embodiment of FIGS. 1 and 3 through 5, both of the exterior surface segments 42' and 44' have a longitudinal curvilinear configuration defined by a longitudinally oriented complex curve including at least a minimally concave portion 49'' and a linear portion 49'''. Similarly, the surface segments 42' and 44' are at least minimally segregated from one another through the provision of the elongated curved edges 46' and 48', extending from the apex 32' towards the base 28' and at least along a majority of the length of the penetrating tip 22'. The edges 46' and 48' may have a more rounded or transversely curved configuration than that of the embodiment of FIG. 3, thereby providing a somewhat "blunted" edge configuration 46' and 48' which, differs from the edge portions 46 and 48 of the embodiment of FIG. 3.

However, the exterior surface 40 of the embodiment of FIGS. 2 and 6 through 8 is structured to define an overall exterior surface configuration shaped to enlarge or at least partially dilate an access opening formed in the outer body wall by the penetrating tip 22', while minimizing any cutting, severing or damaging of the contiguous bodily tissue surrounding the formed access opening. Such a preferred structural configuration is further demonstrated in FIGS. 8B, 8C and 8D which represent a transverse circumferential configuration of the exterior surface 40 as also being substantially elliptical, within the intended meaning of this term, as has been described herein.

Figure 8A:
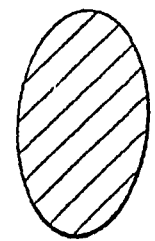
FIG. 8A, 8B, 8C, and 8D are sectional views of the embodiment shown in FIG. 8 and taken along lines 8A-8A, 8B-8B, 8C-8C, and 8D-8D, respectively.
Figure 8B:
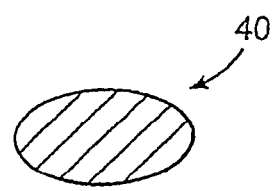
Figure 8C:
Figure 8D:
Figure 6:
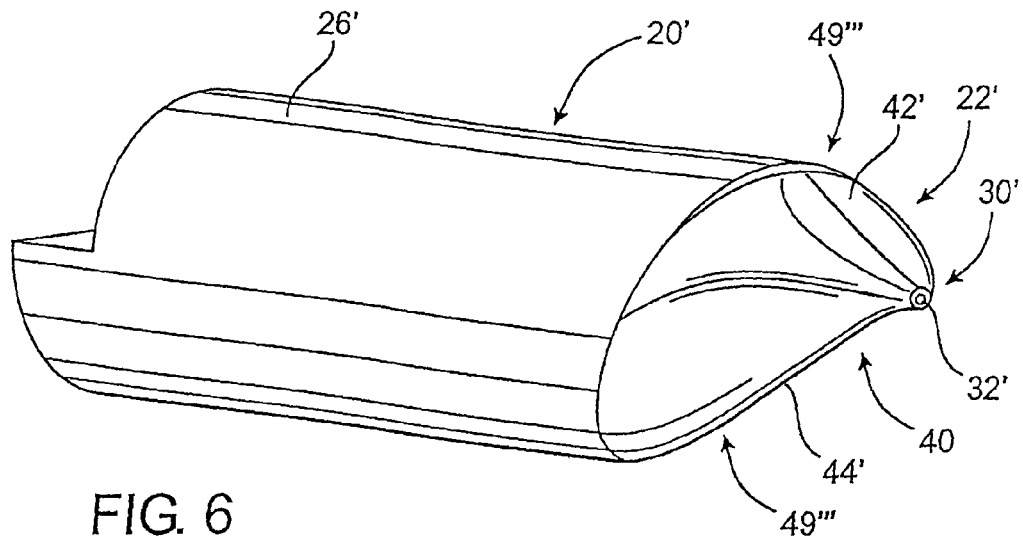
FIG. 6 is a perspective view of yet another embodiment of a penetrating instrument, similar to that of FIG. 2, but shown in partial cutaway to better illustrate the penetrating tip associated therewith.
Figure 7:
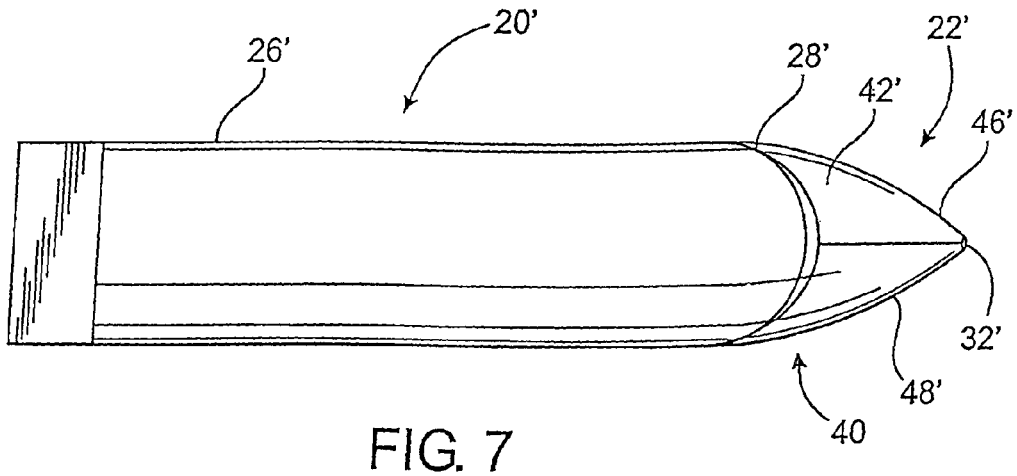
FIG. 7 is a top view in partial cutaway of the embodiment of FIG. 6.
Figure 8:
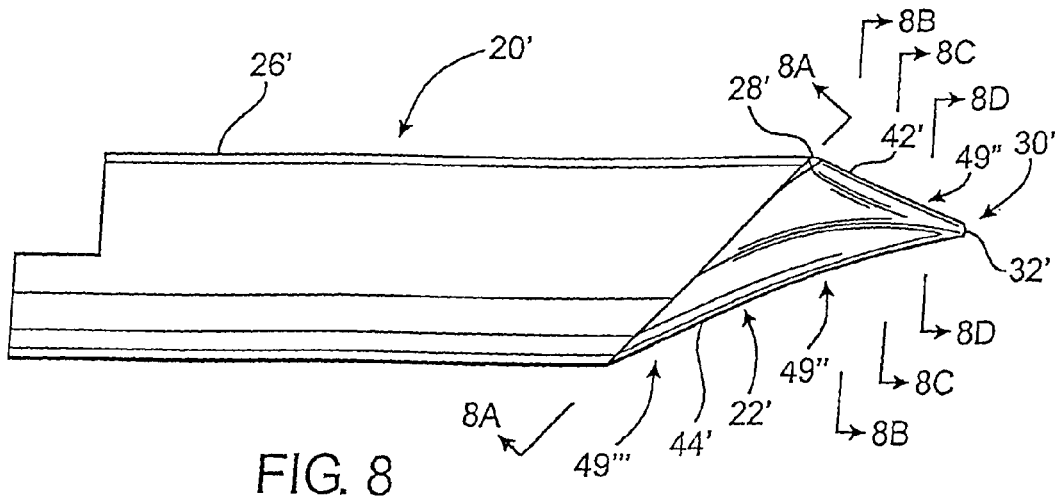
FIG. 8 is a side view in partial cutaway of the embodiment of FIGS. 6 and 7.

As with the embodiment of FIGS. 1 and 3 through 5, the opposite ends of the representative elliptical configurations of the perpendicular cross-sections of the penetrating tip 22' shown in FIGS. 8B, 8C, and 8D, may be more precisely represented by narrowing the opposite ends to more accurately represent the edges 46' and 48'. Also, since the apex 32' is laterally off-set from the central longitudinal axis of the shaft 26', the apex 32' is not centered or centrally coincident with any of the elliptically configured cross-sections represented in FIGS. 8A through 8D. To the contrary, in the embodiment of FIG. 5, the apex 32 is coincident to the linear extension of the central longitudinal axis of the shaft 26 and would therefore be substantially centered relative to the circular cross-section of the base 28, as shown in FIG. 5A, as well as the elliptically configured cross-sections of FIGS. 5B through 5D.

Another preferred embodiment of the penetrating instrument of the present invention is shown in FIGS. 9 through 12 and comprises an obturator 60 including an elongated shaft 62 having a penetrating tip 64 integrally formed with or otherwise secured to the distal end of shaft 62. Penetrating tip 64 includes a base 66, which in the preferred embodiments of FIGS. 9 through 12, is extended along a predetermined angular orientation of generally about 45 degrees relative to a central longitudinal axis of the shaft 62, schematically indicated as 68 in FIG. 10. The base 66 is integrally or otherwise attached to the distal end of the elongated shaft 62, as shown. The opposite end of the penetrating tip 64 terminates in a distal extremity generally indicated as 70, and more specifically, defined by an apex 72. One feature of this embodiment is the disposition of the apex 72 coincident with the central longitudinal axis 68 of the shaft 62, or more precisely, a linear extension 68' of the central longitudinal axis 68.

Additional structural features of this preferred embodiment include the exterior surface 74 including longitudinally extending, curved exterior surface segments 76 and 78. Due at least in part to the angular orientation of the base 66, the exterior surface segments 76 and 78 have different lengths, as best shown in FIG. 10, and are non-symmetrical even though the apex 72 is disposed coincident with the central longitudinal axis 68 or the linear extension thereof 68'.

Figure 10:
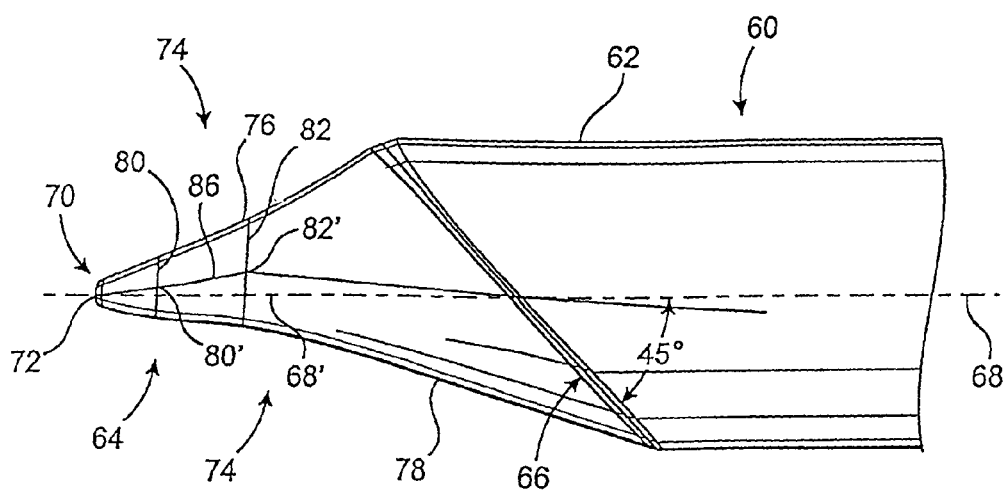
FIG. 10 is a side view of the embodiment of FIG. 9.
Figure 11:
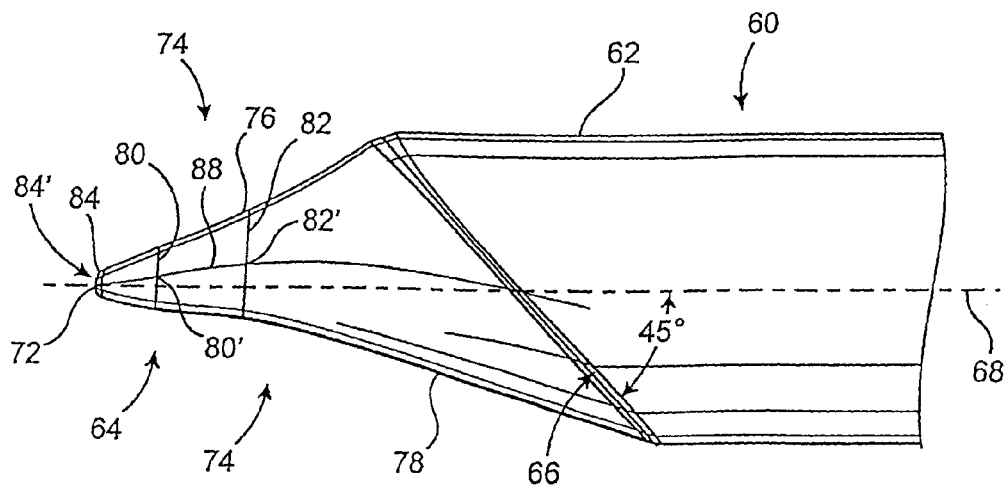
FIG. 11 is a side view of a structural variation of the embodiment of FIG. 10.
Figure 12:
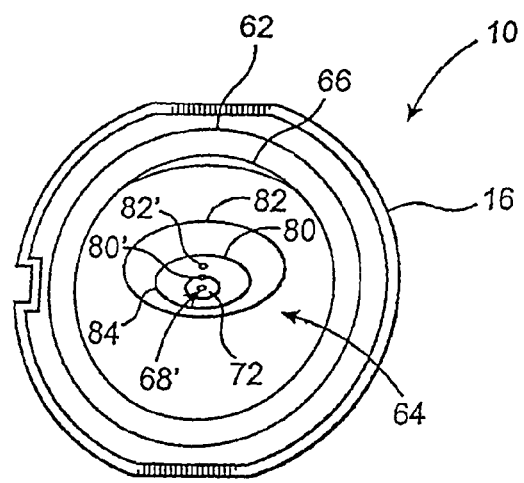
FIG. 12 is a front end view of the embodiment of FIGS. 9 through 11.

Referring now to both FIGS. 10 and 11, the exterior surface 74 of the penetrating tip 64, particularly including the exterior surface segments 76 and 78, can define an at least partially concave, convex and/or complex, longitudinal extending curve(s). As a result, the perpendicular cross-sectional configuration of the penetrating tip 64, such as along schematic cross-section lines 80 and 82, comprises a substantially elliptical configuration. These elliptical configurations of sections 80 and 82 are also meant to be schematically representative of a variety of different shapes intended to be included within the meaning of the generic term "substantially elliptical," as has already been discussed in detail.

As noted, structural differences of the embodiment of FIGS. 9 through 12 include the apex 72 being coincident with the longitudinal axis 68, 68' of the shaft 62, rather than being off-set therefrom. In addition, the complex curve of at least one of the exterior surface segments 76 or 78 would preferably include an elongated concave configuration extending from the apex 70 to towards the base 66 in order to facilitate the penetrating capabilities of the penetrating tip 64. A concave configuration of one or both of the exterior surface segments 74 and 76 may be important, especially when the apex 72 assumes a more blunted shape as opposed to a sharpened point. It is further emphasized that the exterior surface 74, including the exterior surface segments 76 and 78 may vary from that shown in FIGS. 10 and 11. Accordingly, dependent upon the configurations of the exterior surface 74, any of an infinite number of perpendicular sections, such as those taken along schematic lines 80 and 82, will have the aforementioned substantially elliptical configuration. Also, the centers as at 80' and 82' of the respective elliptical configurations as shown in FIGS. 10 and 11 may be disposed along an imaginary straight line as at 86 and/or along an imaginary curved line as at 88.

As set forth above, the apex 72 may be somewhat blunted rather than a true sharpened point, and thereby, as illustrated in FIG. 11, be at least partially defined by an end ellipse 84. Again, the location of the centers 80' and 82' as well as the center 84' of the end ellipse 84 may be disposed along a straight line 86 or a curved line 88 depending, at least in part, on the overall exterior surface configuration 74, while the apex and/or the center point 84' of the end ellipse 84 remains coincident with the longitudinal axis 68, 68'. Naturally, as with the embodiments of FIGS. 1 through 8, the obturator 60 may be of the type to be used in combination with a trocar assembly generally indicated as 10 including the elongated trocar sleeve 16 as shown in both FIGS. 1 and 12.

Figure 9:
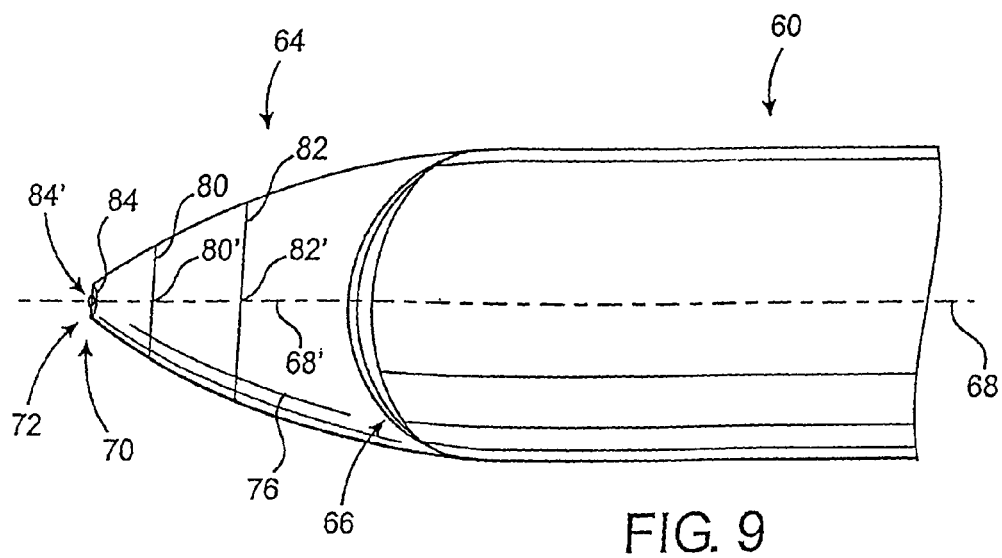
FIG. 9 is a top view of another embodiment of a penetrating instrument according to the present invention including a penetrating tip and associated shaft, in partial cutaway.

Still referring to the embodiment(s) shown in FIGS. 9 through 11, it is noted that the base 66, being angularly oriented at a preferred angle of 45 degrees relative to the longitudinal axis 68 and 68', defines an elliptical configuration somewhat similar to that shown in the embodiment of FIG. 8A. The precise shape of the preferred elliptical configuration will, of course, vary, dependent on the angular orientation of the base 66 relative to the longitudinal axis 68 being greater or less than the preferred 45 degree angle of incline, as indicated.

Figure 14:
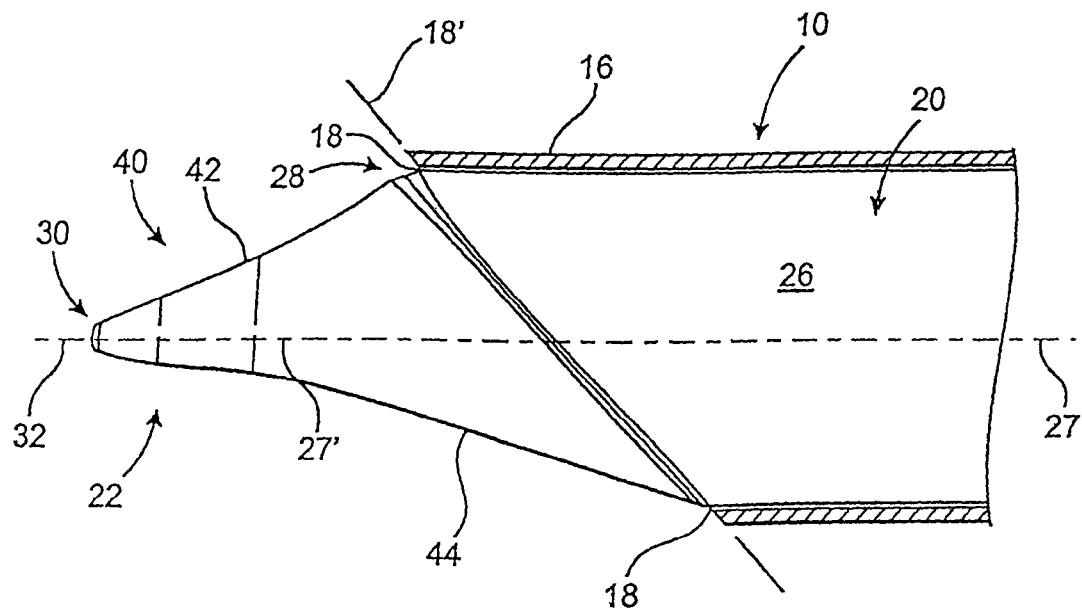
FIG. 14 is a longitudinal view in partial section and cutaway of yet another preferred embodiment of the present invention showing the penetrating tip in an operative position relative to a trocar sleeve.
Figure 15:
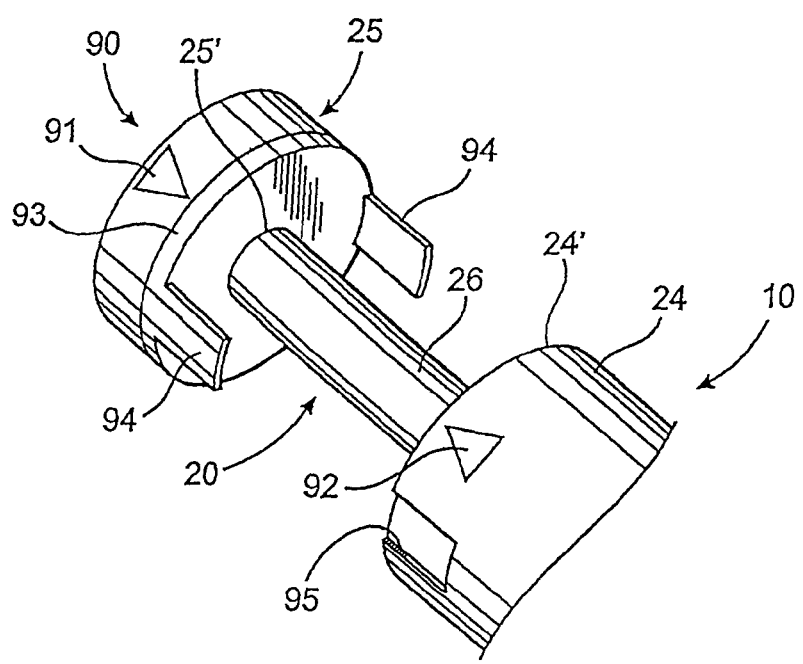
FIG. 15 is a perspective view in partial cutaway of yet another preferred embodiment of the present invention directed to structural components associated with a trocar assembly embodying the instrument of the present invention.

Another feature of at least one preferred embodiment of the present invention is shown in FIG. 14, wherein the laparoscopic instrument is embodied in a trocar assembly 10 having a trocar sleeve 16 with an open distal end 18. As will also be explained with regard to the embodiment of FIG. 15, the elongated shaft 26 is positioned within the interior passage of the sleeve 16 and is longitudinally dimensioned to facilitate the positioning of the penetrating tip 22 in an operative position having a most preferred orientation. This operative position is at least partially defined by the penetrating tip 22 being disposed in a "closing" relation to the open distal end 18 so as to restrict or block the passage of any unwanted material, such as body tissue, from passing through the open distal end 18 into the interior of the sleeve 16. The aforementioned operative position may be further defined by the penetrating tip 22, and more specifically, the base 28 thereof, having a common angular orientation relative to the open distal end 18, or more specifically the plane defined by the open distal end 18, as schematically represented by the plane or section line 18'.

Accordingly, when the penetrating tip 22 is in the aforementioned operative position, the base 28 of the penetrating tip 22 is substantially aligned with the open end 18 and the plane 18' defined thereby. The closing or blocking relation between the base 28 and the open end 18 is facilitated by the base having a somewhat common transverse dimension to the open end 18, thereby effectively filling, blocking or closing the open end 18, when the penetrating tip 22 is in the preferred, operative position, as shown in FIG. 14. Further, in this preferred embodiment the base 28 of the penetrating tip 22 is disposed at a predetermined angular orientation relative to the central axis 27 of the shaft 26. This angular orientation corresponds to substantially the same angular orientation of the plane of the open distal end 18, schematically demonstrated by the plane or section line 18'. Therefore, the aforementioned operative position of the penetrating tip 22 may be further defined by the penetrating tip 22, and more specifically, the base 28 being oriented at the same angle of inclination as the open end 18.

As set forth above, the obturator 20 and in particular, the elongated shaft 26 is selectively positioned within the interior passage or lumen of the trocar sleeve 16. The shaft 26 can be rotated within, as well as longitudinally positioned within the interior of the sleeve 16. In order to properly position the shaft 26 relative to the sleeve 16 such that the operative position of the penetrating tip 22 is accomplished, the shaft 26 includes the aforementioned gripping portion 25 secured or otherwise connected to the proximal end 25' thereof. To facilitate a precise positioning of the shaft 26, in a manner which is convenient to a surgeon, the present invention includes an indexing assembly, generally indicated as 90, which is preferably mounted at least partially on the gripping portion 25 and partially on the mounting hub 24. As set forth above, the mounting hub 24 may be connected to the trocar housing and/or may at least partially defines the proximal end of the trocar sleeve 16. More specifically, the indexing assembly 90 includes a first indexing member 91 and a second indexing member 92 respectively formed on the gripping portion 25 and the mounting hub 24. When the trocar assembly 10 is in use, the physician or other medical personnel places the elongated shaft 26 on the interior of the trocar sleeve 16 while exerting a pushing and/or rotating force on the gripping portion 25. Proper angular alignment between the penetrating tip 22 and the sleeve 16, and more specifically, between the base 28 and the plane 18' of the open distal end 18 is accomplished when the first and second indexing members 91 and 92 are brought into aligned registry with one another.

Further structural features of this preferred embodiment includes the provision of a stop structure. As set forth above, the longitudinal dimension of the shaft 26 is such as to dispose the penetrating tip 22 in the aforementioned operative position as demonstrated in FIG. 14. The operative position is at least partially obtained when the shaft 26 is fully extended through the mounting hub 24, trocar housing 12 and remainder of the sleeve 16. To facilitate proper positioning of the shaft 26 in this manner, a stop member as at 93 is mounted on the positioning member 25. The stop member 93 is disposed to abut and come into "stopping" engagement with a portion of the mounting hub 24, such as about the periphery thereof as at 24'.

Accordingly, when indexing members 91 and 92 are aligned in the manner set forth above and when the stop member 93 engages the predetermined, interruptive portion of the proximal end of the sleeve 16, such as the periphery 24' of the mounting hub 24, the medical personnel are sure that the instrument is operatively assembled and that the penetrating tip 22 is in the aforementioned operative position.

A connecting or locking assembly may also be included and may comprise one or more connecting or locking tabs 94, which may be biased due to the structure or the material from which the tabs 94 are formed. The connecting tabs 94 are disposed and dimensioned to be removably received within connecting compartments or recesses 95 correspondingly disposed within the hub 24 or other portion of the proximal end of the trocar sleeve 16, dependent on the type of the trocar assembly 10, 10' etc. being utilized.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described.

What is claimed is:

1. An instrument comprising:
    a trocar sleeve having an open distal end;
    an obturator being movably disposed within said trocar sleeve and including a penetrating tip disposed at one end thereof, said obturator including a central longitudinal axis, said penetrating tip comprising a blunted apex, a base and an exterior surface extending longitudinally between said base and said apex; and
    a cross section of said penetrating tip taken along said central longitudinal axis substantially transversely thereof between said apex and said base having a dimension of said cross-section in at least one direction which is greater than another dimension of said cross section in another direction substantially perpendicular to said one direction, further comprising at least two curved surface segments formed on said exterior surface and extending longitudinally between said apex and said base, wherein said penetrating tip comprises at least two curved segregating edges extending longitudinally along said exterior surface between said apex and said base, said curved segregating edges each having a blunted edge configuration disposed between and connecting said two curved surface segments, said blunted edge configuration extending at least from said apex towards said base.

2. An instrument comprising:
    a trocar sleeve having an open distal end;
    an obturator being movably disposed within said trocar sleeve and including a penetrating tip disposed at one end thereof, said obturator including a central longitudinal axis, said penetrating tip comprising a blunted apex, a base and an exterior surface extending longitudinally between said base and said apex; and
    a cross section of said penetrating tip taken along said central longitudinal axis substantially transversely thereof between said apex and said base having a dimension in at least one direction which is greater than a dimension of said cross section in another direction substantially perpendicular to said one direction, further comprising at least two curved surface segments formed on said exterior surface and extending longitudinally between said apex and said base, wherein said penetrating tip comprises at least two curved segregating edges extending longitudinally along said exterior surface between said apex and said base, said curved segregating edges each having a blunted edge configuration disposed between said two curved surface segments, said blunted edge configuration extending at least from said apex towards said base, and
    wherein the exterior surface of said penetrating tip tapers continuously from the base to converge at the apex and wherein at least a portion of said exterior surface has a concave shape extending in a longitudinal direction, and a convex shape extending in a direction generally transverse to said longitudinal axis of said obturator.

3. An instrument as recited in claim 2, wherein said curved segregating edges are connecting said two curved surface segments to form a smooth continuous outer circumference of said cross section.

* * * * *